United States Patent [19]

Rizkalla

[11] Patent Number: 4,625,055
[45] Date of Patent: * Nov. 25, 1986

[54] PREPARATION OF CARBOXYLIC ACIDS
[75] Inventor: Nabil Rizkalla, River Vale, N.J.
[73] Assignee: The Halcon SD Group, Inc., Little Ferry, N.J.
[*] Notice: The portion of the term of this patent subsequent to Oct. 12, 1999 has been disclaimed.
[21] Appl. No.: 741,030
[22] Filed: Jun. 3, 1985

Related U.S. Application Data
[63] Continuation of Ser. No. 431,451, Sep. 30, 1982, abandoned.
[51] Int. Cl.$^4$ .............................................. C07C 51/14
[52] U.S. Cl. ................................... 562/406; 562/497; 562/522; 260/413; 560/114; 560/233

[58] Field of Search .................... 562/406, 497, 522; 260/413; 560/233, 114

[56] References Cited
U.S. PATENT DOCUMENTS
4,354,036 10/1982 Rizkalla .............................. 560/232

Primary Examiner—Werren B. Lone
Attorney, Agent, or Firm—Harold N. Wells

[57] ABSTRACT

A carboxylic acid, such as propionic acid, is prepared by carbonylation of an olefin, such as ethylene in the presence of water by the use of a molybdenum-nickel-alkali metal, tungsten-nickel alkali metal, or chromium-nickel-alkali metal co-catalyst in the presence of a halide.

4 Claims, No Drawings

PREPARATION OF CARBOXYLIC ACIDS

This case is a continuation of Ser. No. 431,451 filed Sept. 30, 1982, now abandoned.

This invention relates to the preparation of carboxylic acids, more particularly mono-carboxylic acids, and especially lower alkanoic acids, such as propionic acid, by the carbonylation of olefins.

Carboxylic acids have been known as industrial chemicals for many years and large amounts are used in the manufacture of various products. Producing carboxylic acids by the action of carbon monoxide upon olefins (carbonylation) has been described, for example, in Reppe et al U.S. Pat. No. 2,768,968. However, such prior proposals involving olefin carbonylation reactions have required the use of very high pressures. Olefin carbonylation processes effective at lower pressures have also been proposed. Craddock et al U.S. Pat. Nos. 3,579,551; 3,579,552 and 3,816,488, for example, describe the carbonylation of olefins in the presence of compounds and complexes of Group VIII noble metals such as iridium and rhodium in the presence of iodide under more moderate pressures than those contemplated by Reppe et al. These lower-pressure carbonylation disclosures, however, require the use of expensive noble metals. More recently, Belgian Pat. No. 860,557 has proposed the preparation of carboxylic acids by carbonylation of alcohols in the presence of a nickel catalyst promoted by a trivalent phosphorus compound and in the presence of an iodide. In my co-pending application Ser. No. 267,963 filed May 28, 1981, and entitled "Preparation of Carboxylic Acids," there is disclosed a related process for the carbonylation of olefins to produce carboxylic acids which uses a molybdenum-nickel or tungsten-nickel co-catalyst in the presence of a promoter comprising an organo-phosphorus or an organo-nitrogen compound. While these processes involving nickel catalysts make possible carbonylation at modest pressures without requiring the use of a noble metal catalyst, there is room for improved reaction rate and productivity, without need for organic promoters.

It is accordingly an object of the present invention to provide an improved process for the manufacture of carboxylic acids, especially lower alkanoic acids, such as propionic acid, which requires neither high pressures nor Group VIII noble metals and makes possible the production of carboxylic acids in high yields in short reaction times without need for organic promoters.

In accordance with the invention, carbonylation of an olefin is carried out by using a molybdenum-nickel-alkali metal, a tungsten-nickel-alkali metal or a chromium-nickel-alkali metal co-catalyst in the presence of a halide, preferably an iodide, a bromide and/or a chloride, especially an iodide, and water. The surprising discovery has been made that this co-catalyst system in an environment of the character indicated makes possible carbonylation of olefins not only at relatively low pressures but with rapid, high yield production of carboxylic acids.

The outstanding effectiveness of the catalyst system of the process of this invention is particularly surprising in view of the experimental data reported in European published application No. 0 035 458 which shows the carbonylation of methanol to produce acetic acid and in which experiments using nickel in combination with molybdenum or tungsten or chromium showed absolutely no reaction even after two hours. It has also been observed that when nickel-based catalysts are ordinarily used in carbonylation reactions, there is a tendency for the nickel components to be volatilized and to appear in the vapors from the reaction. It has been surprisingly found that, with the catalyst system of this invention, the volatility of the nickel is strongly suppressed and a highly-stable catalyst combination results, especially in the case of the molybdenum-containing co-catalyst, which is the preferred co-catalyst.

Thus, in accordance with the invention, carbon monoxide is reacted with an olefin such as a lower alkene to produce a carboxylic acid, such as a lower alkanoic acid, the carbonylation taking place in the presence of a halide, e.g., a hydrocarbyl halide, especially a lower alkyl halide, such as ethyl iodide, in the presence of water and in the presence of the co-catalyst which has been identified above. Propionic acid, for example, can be effectively prepared in a representative case by subjecting ethylene to carbonylation.

In like manner, other alkanoic acids, such as butyric acid and valeric acid, can be produced by carbonylating the corresponding lower alkene such as propylene, butene-1, butene-2, the hexenes, the octenes, and the like. Similarly, other alkanoic acids, for example, capric acid, caprylic acid, and lauric acid, and like higher carboxylic acids are produced by carbonylating the corresponding olefin.

The reactant olefin may be any ethylenically unsaturated hydrocarbon having from 2 to about 25 carbon atoms, preferably from 2 to about 15 carbon atoms. The ethylenically unsaturated compound has the following general structure:

$$R_2R_1C=CR_3R_4$$

wherein $R_1$, $R_2$, $R_3$ and $R_4$ are hydrogen or the same or different alkyl, cycloalkyl, aryl, alkaryl, aralkyl or wherein one of said $R_1$ and $R_2$ and one of said $R_3$ and $R_4$ together form a single alkylene group having from 2 to about 8 carbon atoms. $R_1$, $R_2$, $R_3$ and $R_4$ can be branched and can be substituted with substituents which are inert in the reactions of the invention.

Examples of useful ethylenically unsaturated hydrocarbons are ethylene, propylene, butene-1, butene-2, 2-methylbutene-1, cyclobutene, hexene-1, hexene-2, cyclohexene, 3-ethylhexene-1, isobutylene, octene-1, 2-methylhexene-1, ethylcyclohexene, decene-1, cycloheptene, cyclooctene, cyclononene, 3,3-dimethylnonene-1, dodecene-1, undecene-3, 6-propyldecene-1, tetradecene-2, 3-amyldecene-1, etc., hexadecene-1, 4-ethyltridecene-1, octadecene-1, 5,5-dipropyldodecene-1, vinylcyclohexane, allylcyclohexane styrene, p-methylstyrene, alpha-methylstyrene, p-vinylcumene, beta-vinylnaphthalene, 1,1-diphenylethylene, allylbenzene, 6-phenylhexene-1, 1,3-diphenylbutene-1, 3-benzylheptene-1, divinylbenzene, 1-allyl-3-vinylbenzene, etc. Of the olefins referred to above, the alpha hydrocarbon olefins and olefins having 2 to about 10 carbon atoms are preferred, e.g., ethylene, propylane, butene-1, hexene-1, heptene-1, octene-1, and the like, i.e., wherein $R_1$, $R_2$, $R_3$ and $R_4$ are hydrogen or alkyl groups totalling 1 to 8 carbon atoms, preferably the lower alkenes, i.e., alkenes of 2 to 6 carbon atoms, especially ethylene.

In the most preferred embodiment of the invention, carbon monoxide is reacted with ethylene and water in the presence of the co-catalyst halide system of the character described above to produce propionic acid in a reaction which may be expressed as follows:

$$C_2H_4 + CO + H_2O \rightarrow C_2H_5COOH$$

Carbon monoxide is removed in the vapor phase along with unreacted olefin when the olefin is normally gaseous, e.g., ethylene, and, if desired, recycled. Normally-liquid and relatively-volatile components such as alkyl halide, normally-liquid unreacted olefin and water, and any by-products present in the final product mixture can be readily removed and separated from each other as by distillation, for recycling, and the net yield of product is substantially exclusively the desired carboxylic acid. In the case of liquid-phase reaction, which is preferred, the organic compounds are easily separated from the metal-containing components, as by distillation. The reaction is suitably carried out in a reaction zone to which the carbon monoxide, the olefin, water, the halide, and the co-catalyst are fed.

As will be apparent from the foregoing equation, a carbonylation reaction of the character described selective to carboxylic acid requires at least one mol of carbon monoxide and one mol of water per mol (equivalent) of ethylenically unsaturated linkage reacted. Thus, the olefin feedstock is normally charged with equimolar amounts of water, although more water may be used.

In carrying out the process of the invention, a wide range of temperatures, e.g., 25° to 350° C. are suitable but temperatures of 100° to 250° C. are preferably employed, and the more preferred temperatures generally lie in the range of 125° to 225° C. Temperatures lower than those mentioned can be used, but they tend to lead to reduced reaction rates, and higher temperatures may also be employed but there is no particular advantage in their use. The time of reaction is also not a parameter of the process and depends largely upon the temperature employed, but typical residence times, by way of example, will generally fall in the range of 0.1 to 20 hours. The reaction is carried out under superatmospheric pressure but as previously mentioned, it is a feature of the invention that excessively high pressures, which require special high-pressure equipment, are not necessary. In general, the reaction is effectively carried out by employing a carbon monoxide partial pressure which is preferably at least 15 but less than 2,000 psi, most preferably 15 to 1,000 psi, and particularly 30 to 200 psi, although CO partial pressures of 1 to 5,000 or even up to 10,000 psi can also be employed. By establishing the partial pressure of carbon monoxide at the values specified, adequate amounts of this reactant are always present. The total pressure is, of course, that which will provide the desired carbon monoxide partial pressure, and preferably it is that required to maintain the liquid phase and, in this case, the reaction can be advantageously carried out in an autoclave or similar apparatus. At the end of the desired residence time, the reaction mixture is separated into its several constituents, as by distillation. Preferably, the reaction product is introduced into a distillation zone which may be a fractional distillation column, or a series of columns, effective to separate the volatile components from the product acid and to separate the product acid from the less volatile catalyst components of the reaction mixture. The boiling points of the volatile components are sufficiently far apart that their separation by conventional distillation presents no particular problem. Likewise, the higher-boiling organic components can be readily distilled away from the metal catalyst components. The thus-recovered co-catalyst, including the halide component, can then be combined with fresh amounts of olefin, carbon monoxide and water and reacted to produce additional quantities of carboxylic acid.

Although not necessary, the process can be carried out in the presence of a solvent or diluent. The presence of a higher-boiling solvent or diluent, preferably the product acid itself, e.g., propionic acid in the case of ethylene carbonylation, will make it possible to employ more moderate total pressures. Alternatively, the solvent or diluent may be any organic solvent which is inert in the environment of the process, such as hydrocarbons, e.g., octane, benzene, toluene, xylene and tetralin, or carboxylic acids. A carboxylic acid, if used, should preferably correspond to the acid being produced since it is preferred that the solvent employed be indigenous to the system, e.g., propionic acid in the case of ethylene carbonylation, although other carboxylic acids such as acetic acid can also be used. A solvent or diluent, when not the product itself, is suitably selected which has a boiling point sufficiently different from the desired product in the reaction mixture so that it can be readily separated, as will be apparent to persons skilled in the art. Mixtures can be used.

The carbon monoxide is preferably employed in substantially pure form, as available commercially, but inert diluents such as carbon dioxide, nitrogen, methane, and noble gases can be present, if desired. The presence of inert diluents does not affect the carbonylation reaction, but their presence makes it necessary to increase the total pressure in order to maintain the desired CO partial pressure. Hydrogen which may be present as an impurity is not objectionable and even may tend to stabilize the catalyst. Indeed, in order to obtain low CO partial pressures, the CO fed may be diluted with hydrogen or any inert gas such as those mentioned above amounts of diluent gas up to 95% can be used.

The co-catalyst components can be employed in any convenient form, viz., in the zero valent state or in any higher valent form. For example, the nickel and the molybdenum, tungsten or chromium can be the metals themselves in finely divided form, or a compound, both organic or inorganic, which is effective to introduce the co-catalyst components into the reaction system. Thus, typical compounds include the carbonate, oxide, hydroxide, bromide, iodide, chloride, oxyhalide, hydride, lower alkoxide (methoxide), phenoxide, or Mo, W, Cr or Ni carboxylates wherein the carboxylate ion is derived from an alkanoic acid of 1 to 20 carbon atoms, such as acetates, butyrates, decanoates, laurates, benzoates, and the like. Similarly, complexes of any of the co-catalyst components can be employed, e.g., carbonyls and metal alkyls as well as chelates, association compounds and enol salts. Examples of other complexes include bis-(triphenylphosphine) nickel dicarbonyl, tricyclopentadienyl trinickel dicarbonyl, tetrakis (triphenylphosphite) nickel, and corresponding complexes of the other components, such as molybdenum hexacarbonyl and tungsten hexacarbonyl.

Particularly preferred are the elemental forms, compounds which are halides, especially iodides, and organic salts, e.g., salts of the monocarboxylic acid corresponding to the acid being produced.

The alkali metal component, e.g., a metal of Group IA of the Periodic Table such as lithium, potassium, sodium, and cesium, is suitably employed as a compound, especially a salt, and most preferably a halide, e.g., an iodide. The preferred alkali metal is lithium. The alkali metal component can, however, also be employed as the hydroxide, carboxylate, alkoxide or in the form of other convenient compounds such as are referred to above in connection with the other co-catalyst components, and typical alkali metal components are illustrated by sodium iodide, potassium iodide, cesium iodide, lithium iodide, lithium bromide, lithium chloride, lithium acetate, and lithium hydroxide.

It will be understood that the above-mentioned compounds and complexes are merely illustrative of suitable forms of the several co-catalyst components and are not intended to be limiting.

The specified co-catalyst components employed may contain impurities normally associated with the commercially available metal or metal compounds and need not be purified further.

The amount of each co-catalyst component employed is in no way critical and is not a parameter of the process of the invention and can vary over a wide range. As is well known to persons skilled in the art, the amount of catalyst used is that which will provide the desired suitable and reasonable reaction rate since reaction rate is influenced by the amount of catalyst. However, essentially any amount of catalyst will facilitate the basic reaction and can be considered a catalytically-effective quantity. Typically, however, each catalyst component is employed in the amount of 1 millimol to 1 mol per liter of reaction mixture, preferably 15 millimoles to 500 millimoles per liter and most preferably 15 millimoles to 150 millimoles per liter.

The ratio of nickel to the molybdenum, tungsten, or chromium co-catalyst component can vary. Typically, it is one mol of the nickel component per 0.01 to 100 mols of the second co-catalyst component, i.e., the molybdenum, tungsten, or chromium component, preferably the nickel component is used in the amount of 1 mol per 0.1 to 20 mols, most preferably 1 mol per 1 to 10 mols of the second co-catalyst component. Similarly, the ratio of nickel to the alkali metal component can vary, e.g., one mol of nickel per 1 to 1000 mols of alkali metal component, preferably 10 to 100 and most preferably 20 to 50.

The amount of halide component may also vary widely but, in general, it should be present in an amount of at least 0.1 mol (expressed as elemental halogen) per mol of nickel. Typically, there are used 1 to 100 mols of the halide per mol of nickel, preferably 2 to 50 mols per mol. Ordinarily, more than 200 mols of halide per mol of nickel are not used. It will be understood, however, that the halide component does not have to be added to the system as a hydrocarbyl halide but may be supplied as another organic halide or as the hydrohalide or other inorganic halide, e.g., a salt, such as the alkali metal or other metal salt, or even as elemental halogen, e.g., iodine or bromine.

As previously mentioned, the catalyst system of this invention comprises a halide, especially an iodide, component and a molybdenum-nickel-alkali metal, tungsten-nickel-alkali metal, or chromium-nickel-alkali metal co-catalyst component. The catalyst system of this invention permits the production of carboxylic acids in high yields in short reaction times without the use of Group VIII noble metals, and the presence of the alkali metal component together with the molybdenum, tungsten or chromium component makes possible good results with relatively small amounts of co-catalyst components and reduced quantities of nickel in comparison with prior art processes involving a nickel-containing catalyst.

A particular embodiment of the catalyst comprising the molybdenum-nickel-alkali metal, tungsten-nickel-alkali metal, or chromium-nickel-alkali metal co-catalyst component and the halide component can be represented by the following formula: $X:T:Z:Q$, wherein X is molybdenum, tungsten or chromium, T is nickel, X and T being in zero valent form or in the form of a halide, an oxide, a carboxylate of 1 to 20 carbon atoms, a carbonyl or an hydride; Z is a halide source which is hydrogen halide, halogen, an alkyl halide wherein the alkyl group contains 1 to 20 carbon atoms or an alkali metal halide, and Q is the alkali metal component. The preferred alkali metal is lithium as previously indicated, and is in the form of an iodide, a bromide, a chloride or a carboxylate as defined for X and T, the molar ratio of X to T being 0.1–10:1, the molar ratio of X + T to Q being 0.1–10:1, and the molar ratio of Z to X + T being 0.01–0.1:1.

It will be apparent that the above-described reaction lends itself readily to continuous operation in which the reactants and catalyst are continuously supplied to the appropriate reaction zone and the reaction mixture continuously distilled to separate the volatile organic constituents and to provide a net product consisting essentially of carboxylic acid with the other organic components being recycled and, in a liquid-phase reaction a residual catalyst containing fraction also being recycled.

It will also be apparent that the catalytic reaction involved in the process of the invention can be carried out in the vapor phase, if desired, by appropriate control of the total pressure in relation to the temperature so that the reactants are in vapor form when in contact with the catalyst. In the case of vapor-phase operation, and in the case of liquid-phase operation, if desired, catalyst components may be supported i.e., they may be dispersed on a carrier of conventional type such as alumina, silica, silicon carbide, zirconia, carbon, bauxite, attapulgus clay, and the like. The catalyst components can be applied to the carriers in conventional manner, e.g., by impregnation of the carrier with a solution of the catalyst component. Concentrations upon the carrier may vary widely, e.g., 0.01 weight percent to 10 weight percent, or higher. Typical operating conditions for vapor-phase operation are a temperature of 100° to 350° C., preferably 150° to 275° C. and most perferably 175° to 255° C., a pressure of 1 to 5,000 p.s.i.a., preferably 59 to 1,500 p.s.i.a. and most preferably 150 to 500 p.s.i.a., with space velocities of 50 to 10,000 hr.$^{-1}$, preferably 200 to 6,000 hr.$^{-1}$ and most preferably 500 to 4,000 hr.$^{-1}$ (STP). In the case of a supported catalyst, the iodide component is included with the reactants and not on the support.

The following examples will serve to provide a fuller understanding of the invention, but it is to be understood that they are given for illustrative purposes only, and are not to be construed as limitative of the invention. In the examples, all parts are by weight, unless otherwise indicated.

EXAMPLE 1

In this example, a magnetically-stirred pressure vessel with a glass liner was employed. The reaction vessel was charged with 12 parts water, 11.9 parts ethyl iodide, 0.76 part nickel iodide (NiI$_2$), 1.4 parts molybdenum hexacarbonyl, 14.3 lithium iodide and 60 parts ethyl acetate as solvent. The vessel was swept out with argon and was pressured to 100 p.s.i.g. with hydrogen and then up to 500 p.s.i.g. with carbon monoxide. The vessel was then heated to 180° C. with stirring. The pressure was brought up to 750 p.s.i.g. with ethylene. The pressure was maintained at 750 p.s.i.g. by recharging a 1:1 mixture of ethylene and carbon monoxide and the temperature was maintained at 180° C. After 1 hour of reaction, G.C. analysis of the reaction mixture showed that propionic acid was formed at the rate of 4.38 mols per liter per hour with all of the olefin reacted appearing as propionic acid.

EXAMPLE 2

A pressure vessel as described in Example 1 was charged with 12 parts water, 12 parts ethyl iodide, 0.74 part nickel iodide (NiI$_2$), 1.4 parts molybdenum hexacarbonyl, 14.4 parts lithium iodide, and 60 parts tetrahydrofuran as solvent. The vessel was swept out with argon and was pressured to 100 p.s.i.g. with hydrogen and then up to 500 p.s.i.g. with carbon monoxide. Then the vessel was heated to 180° C. with stirring and the pressure was brought up to 800 p.s.i.g. with ethylene. The pressure was maintained at 800 p.s.i.g. by recharging a 1:1 mixture of ethylene and carbon monoxide and the temperature was maintained at 80° C. After 1 hour of reaction, G.C. analysis of the reaction mixture showed propionic acid had been formed at the rate of 2.97 mols per liter per hour with all of the olefin reacting appearing as propionic acid.

EXAMPLE 3

A pressure vessel as described in Example 1 was charged with 12 parts water, 12 parts iodoethane, 0.72 part nickel iodide (NiI$_2$), 1.4 parts chromium hexacarbonyl, 14.3 lithium iodide and 60 parts tetrahydrofuran as solvent. The vessel was swept out with argon and was pressured to 100 p.s.i.g. with hydrogen and then up to 500 p.s.i.g. with carbon monoxide. The vessel was heated to 180° C. with stirring and the pressure was brought up to 900 p.s.i.g. using ethylene. The pressure was maintained at 900 p.s.i.g. by recharging a 1:1 mixture of ethylene and carbon monoxide. The temperature was maintained at 180° C. After 1 hour of reaction, G.C. analysis of the reaction mixture showed propionic acid had been formed at the rate of 1.21 mols per liter per hour and that all of the olefin reacted had been converted to propionic acid.

EXAMPLE 4

A magnetically-stirred pressure vessel with a glass liner was charged with 12 parts water, 12 parts ethyl iodide, 0.72 part nickel iodide (NiI$_2$), 1.43 parts molybdenum hexacarbonyl and 14 parts lithium iodide and 60 parts tetrahydrofuran as solvent. The vessel was swept out with argon and pressured to 300 p.s.i.g. with carbon monoxide. The vessel was then heated to 180° C. with stirring and the pressure was brought up to 750 p.s.i.g. with ethylene. The pressure was maintained at 750 p.s.i.g. by recharging a 1:1 mixture of ethylene and carbon monoxide and the temperature was maintained at 180° C. After 1 hour of reaction, G.C. analysis of the reaction mixture showed that propionic acid had been formed at rate of 4.63 mols per liter per hour and that all of the olefin reacted had been converted to propionic acid.

EXAMPLE 5

Example 4 was repeated with the exception that the molybdenum carbonly was replaced with an equal amount of tungsten carbonyl. After 1 hour of reaction, G.C. analysis showed propionic acid had been formed at the rate of 2.6 mols per liter per hour and that all of the ethylene reacted had been converted to propionic acid.

EXAMPLE 6

Using a reactor as described in Example 1, the vessel was charged with 11.4 parts water, 11.4 parts ethyl iodide, 0.7 part nickel iodide (NiI$_2$), 1.4 parts molybdenum hexacarbonyl, 18 parts lithium iodide, and 57 parts tetrahydrofuran as solvent. The vessel was swept out with argon and was pressured with 100 p.s.i.g. of ethylene and then up to 600 p.s.i.g. with carbon monoxide. The vessel was then heated to 180° C. with stirring and the pressure was maintained at 750 p.s.i.g. by recharging a 1:1 mixture of ethylene and carbon monoxide. The temperature was maintained at 180° C. After ½ hour of reaction, G.C. analysis of the reaction mixture showed that propionic acid had been formed at the rate of 6.3 mols per liter per hour and that all of the ethylene reacted had been converted to propionic acid.

EXAMPLE 7

A reactor as described in Example 1 was charged with 12 parts water, 12 parts ethyl iodide, 0.7 part nickel iodide, 1.4 parts molybdenum hexacarbonyl, 14 parts cesium iodide, and 60 parts tetrahydrofuran as solvent. The vessel was swept out with argon and was pressured to 100 p.s.i.g. with hydrogen and then up to 500 p.s.i.g. with carbon monoxide and was heated to 180° C. with stirring. The pressure was raised to 900 p.s.i.g. using ethylene and the pressure was maintained at 900 p.s.i.g. by recharging a 1:1 mixture of ethylene and carbon monoxide. The temperature was maintained at 180° C. After 1 hour of reaction, G.C. analysis of the reaction mixture showed that propionic acid had been formed at the rate of 1.7 mols per liter per hour and that all of the ethylene reacted had been converted to propionic acid.

COMPARATIVE EXAMPLE

Example 2 was repeated with the exception that no molybdenum was charged. After 1 hour of reaction, G.C. analysis showed that the rate of propionic acid formation was only 0.12 mol per liter per hour.

What is claimed is:

1. A process for the preparation of a carboxylic acid which comprises reacting an ethylenically unsaturated compound having the general structure R$_2$R$_1$C=CR$_3$R$_4$ wherein, R$_1$, R$_2$, R$_3$ and R$_4$ are hydrogen or the same or different alkyl or cycloalkyl, or wherein one of said R$_1$ and R$_2$ and one of said R$_3$ and R$_4$ together form a single alkylene group having from 2 to about 8 carbon atoms with carbon monoxide in the presence of water, in the presence of a molybdenum-nickel-alkali metal, a tungsten-nickel-alkali metal or a chromium-nickel-alkali metal co-catalyst component, and being free from organic promoters selected from the group consisting of organo-phosphorus compounds and organo-nitrogen compounds and in the presence of a halide.

2. A process as defined in claim 1, wherein the co-catalyst is molybdenum-nickel-alkali metal.

3. A process as defined in claim 1, wherein the alkali metal is lithium.

4. A process as defined in claim 3, wherein the co-catalyst is molybdenum-nickel-lithium.

* * * * *